United States Patent
Francischelli et al.

(10) Patent No.: US 6,827,715 B2
(45) Date of Patent: Dec. 7, 2004

(54) SYSTEM AND METHOD OF PERFORMING AN ELECTROSURGICAL PROCEDURE

(75) Inventors: David Francischelli, Anoka, MN (US); Rahul Mehra, Stillwater, MN (US); Alison Lutterman, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 18 days.

(21) Appl. No.: 10/056,806

(22) Filed: Jan. 25, 2002

(65) Prior Publication Data
US 2003/0144653 A1 Jul. 31, 2003

(51) Int. Cl.⁷ .............................................. A61B 18/18
(52) U.S. Cl. .......................................... 606/34; 606/41
(58) Field of Search ..................... 606/32–34, 38–42; 607/101, 102

(56) References Cited

U.S. PATENT DOCUMENTS

| | | |
|---|---|---|
| 1,735,271 A | 11/1929 | Groff |
| 4,326,529 A | 4/1982 | Doss et al. |
| 4,920,982 A | 5/1990 | Goldstein |
| 5,151,102 A | 9/1992 | Kamiyama et al. |
| 5,156,613 A | 10/1992 | Sawyer |
| 5,167,659 A | 12/1992 | Ohtomo et al. |
| 5,217,460 A | 6/1993 | Knoepfler |
| 5,300,087 A | 4/1994 | Knoepfler |
| 5,318,589 A | 6/1994 | Lichtman |
| 5,348,554 A | 9/1994 | Imran et al. |
| 5,364,394 A | 11/1994 | Mehl |
| 5,383,874 A | * 1/1995 | Jackson et al. ............... 606/1 |
| 5,395,312 A | 3/1995 | Desai |
| 5,395,363 A | 3/1995 | Billings et al. |
| 5,401,272 A | 3/1995 | Perkins |
| 5,403,312 A | 4/1995 | Yates et al. |
| 5,431,649 A | 7/1995 | Mulier et al. |
| 5,458,596 A | 10/1995 | Lax et al. |
| 5,458,598 A | 10/1995 | Feinberg et al. |
| 5,472,441 A | 12/1995 | Edwards et al. |
| 5,487,385 A | 1/1996 | Avitall |
| 5,569,242 A | 10/1996 | Lax et al. |
| 5,584,872 A | 12/1996 | LaFontaine et al. |
| 5,609,151 A | 3/1997 | Mulier et al. |
| 5,647,871 A | 7/1997 | Levine et al. |
| 5,688,267 A | * 11/1997 | Panescu et al. ............... 606/41 |
| 5,697,927 A | 12/1997 | Imran et al. |
| 5,718,701 A | 2/1998 | Shai et al. |
| 5,725,524 A | 3/1998 | Mulier et al. |
| 5,733,280 A | 3/1998 | Avitall |
| 5,782,828 A | 7/1998 | Chen et al. |
| 5,797,960 A | 8/1998 | Stevens et al. |
| 5,827,271 A | 10/1998 | Buysse et al. |
| 5,853,411 A | * 12/1998 | Whayne et al. ............... 606/41 |

(List continued on next page.)

FOREIGN PATENT DOCUMENTS

| | | |
|---|---|---|
| WO | WO 96/34567 | 11/1996 |
| WO | WO 01/68173 | 9/2001 |
| WO | WO 01/80757 | 11/2001 |

*Primary Examiner*—Michael Peffley
(74) *Attorney, Agent, or Firm*—Thomas G. Berry; Jeffrey J. Hohenshell (57) ABSTRACT

A system and method of making a lesion on living tissue including providing an electrosurgical system, determining a desired lesion depth, selecting a power setting, and applying electrical energy to the living tissue. The system includes an instrument having an electrode at a distal portion thereof, and a power source having multiple available power settings. The power source is electrically connected to the electrode. The step of applying electrical energy includes energizing the electrode at the selected power setting for a recommended energization time period that is determined by reference to predetermined length of time information and based upon the desired lesion depth and the selected power setting. The system preferably further includes a fluid source for irrigating the electrode at an irrigation rate. In this regard, the predetermined length of time information is generated as a function of irrigation rate.

34 Claims, 4 Drawing Sheets

U.S. PATENT DOCUMENTS

| | | | | |
|---|---|---|---|---|
| 5,897,553 A | * | 4/1999 | Mulier et al. | 606/41 |
| 5,925,038 A | | 7/1999 | Panescu et al. | |
| 5,951,546 A | | 9/1999 | Lorentzen | |
| 5,964,755 A | | 10/1999 | Edwards | |
| 5,971,980 A | * | 10/1999 | Sherman | 606/34 |
| 6,009,877 A | * | 1/2000 | Edwards | 128/898 |
| 6,096,037 A | | 8/2000 | Mulier et al. | |
| 6,113,592 A | | 9/2000 | Taylor | |
| 6,175,768 B1 | | 1/2001 | Arndt et al. | |
| 6,217,573 B1 | | 4/2001 | Webster | |
| 6,237,605 B1 | | 5/2001 | Vaska et al. | |
| 6,358,248 B1 | | 3/2002 | Mulier et al. | |
| 6,443,952 B1 | | 9/2002 | Mulier et al. | |
| 6,475,216 B2 | | 11/2002 | Mulier et al. | |
| 6,502,575 B1 | | 1/2003 | Jacobs et al. | |

* cited by examiner

SYSTEM AND METHOD OF PERFORMING AN ELECTROSURGICAL PROCEDURE

BACKGROUND OF THE INVENTION

The present invention relates to a system and method of performing an electrosurgical procedure using an electrosurgical (ablation or electrocautery) device. More particularly, it relates to a method of performing an electrosurgical procedure using an ablation or electrocautery system to create a lesion.

A wide variety of surgical procedures involve ablation or cauterization of selected tissue. For example, hemorrhoid or varicose vein removal can be accomplished by ablating the tissue in question. Additionally, tissue ablation and/or cauterization is commonly employed for the surgical treatment of cardiac arrhythmia and, in particular, atrial fibrillation. In general terms, cardiac arrhythmia relates to disturbances in the heart's electrical system that causes the heart to beat irregularly, too fast or too slow. Irregular heartbeats, or arrhythmia, are caused by psychological or pathological disturbances in the discharged electrical impulses from the sinoatrial node, and the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. As to the location of the depolarizing tissue, it is generally agreed that the undesired electrical impulses often originate in the left atrial region of the heart, and in particular in one (or more) of the pulmonary veins extending from the left atrium. With this in mind, and as an alternative to drug therapy, ablation of the abnormal tissue or accessory pathway responsible for the atrial fibrillation has proven highly viable.

Regardless of exact application, ablation or cauterization of tissue is typically achieved by applying a destructive energy source to the target tissue, including radiofrequency electrical energy, direct current electrical energy, and the like. The ablative energy source is provided by an electrode and is otherwise placed in contact with the target tissue. The electrode can be formed as part of a handheld electrosurgical instrument. As used herein, the term "electrosurgical instrument" includes a handheld instrument capable of ablating or cauterizing tissue. The instrument rigidly couples the electrode tip to an instrument handle that is otherwise held and manipulated by the surgeon. The rigid construction of the electrosurgical instrument typically requires direct, open access to the target tissue. Thus, for treatment of atrial fibrillation via an electrosurgical instrument, it is desirable to gain access to the patient's heart through one or more openings in the patient's chest (such as a sternotomy, a thoractomy, a small incision and/or a port). In addition, the patient's heart may be opened through one or more incisions, thereby allowing access to the endocardial surface of the heart.

Once the target site (e.g., right atrium, left atrium, endocardial surface, epicardial surface, etc.) is accessible, the surgeon positions the electrode tip of the electrosurgical instrument at the target site. The tip is then energized, ablating (or for some applications, cauterizing) the contacted tissue. A desired lesion pattern is then created (e.g., portions of a known "Maze" procedure) and moving the tip in a desired fashion along the target site. In this regard, the surgeon can easily control positioning and movement of the tip, as the electrosurgical instrument is rigidly constructed and relatively short.

Electrosurgical instruments, especially those used for treatment of atial fibrillation, have evolved to include additional features that provide improved results for particular procedures. For example, U.S. Pat. No. 5,897,553, the teachings of which are incorporated herein by reference, describes a fluid-assisted electrosurgical instrument that delivers a conductive solution to the target site in conjunction with electrical energy, thereby creating a "virtual" electrode. The virtual electrode technique has proven highly effective at achieving the desired ablation while minimizing collateral tissue damage. Other electrosurgical instrument advancements have likewise optimized system performance. Unfortunately, however, use of the electrosurgical instrument to produce a lesion having desired characteristics has remained a lengthy and intense procedure.

Typically, a lesion is created by repeatedly drawing the electrosurgical instrument across the target tissue site. Before, during, and after each pass of the electrosurgical instrument across the target tissue site, the tissue is carefully monitored and tested to determine the depth of lesion penetration on the target tissue site. Monitoring and testing of the site ensure the proper number of passes of the electrosurgical instrument to create a lesion having the desired depth for a particular procedure.

Although creating a lesion by repeatedly drawing the electrosurgical instrument across a target tissue site is an effective method, the need for constant monitoring and testing increases the length of time required to perform the procedure. Overall procedure time is critical to the safety of the surgery. For example, a prolonged surgical treatment for atrial fibrillation increases the length of time the heart is stopped and opened and, consequently, increases the chance of complication and infection. As a result, advancements are needed to decrease the time of such electrosurgical procedures.

Electrosurgical procedures utilizing electrosurgical instruments remain a viable method of lesion production for a variety of surgical treatments, including the surgical treatment of atrial fibrillation. However, typical procedures require prolonged operation time due to the need for constant testing and monitoring of the tissue and lesion depth. Therefore, a need exists for an electrosurgical procedure that reduces reliance upon testing and monitoring during the procedure, and thereby reduces procedure time and the risk of complication.

SUMMARY OF THE INVENTION

One aspect of the present invention relates to a method of making a lesion on living tissue at a target site. The method includes providing an electrosurgical system, determining a desired lesion depth, selecting a desired power setting, and applying electrical energy to the living tissue. The electrosurgical system includes an electrosurgical instrument having an electrode at a distal portion thereof, and a power source having multiple available power settings. The power source is electrically connected to the electrode. The step of applying electrical energy includes energizing the electrode, via the power source, at the selected power setting for a recommended energization time period that is determined by reference to predetermined length of time information and based upon the desired lesion depth and the selected power setting. In one preferred embodiment, the predetermined length of time information is embodied in a look-up table. In another preferred embodiment, the electrosurgical system further includes a fluid source maintaining a supply of fluid. The fluid source is fluidly connected to the electrosurgical instrument and is configured to irrigate the electrode at an irrigation rate. In this regard, the predetermined length of time information is generated as a function of irrigation rate.

Another aspect of the present invention relates to an electrosurgical system for performing an electrosurgical procedure on living tissue. The electrosurgical system includes an electrosurgical instrument having an electrode at a distal portion thereof, a power source having multiple available power settings, and an energization look-up table. The power source is electrically connected to the electrosurgical instrument for selectively energizing the electrode. The energization look-up table includes a power setting data set, a lesion depth data set, and a corresponding energization time period information that is organized as a function of the power setting and lesion depth data sets. The energization time period information is adapted to identify a recommended energization time period for a particular electrosurgical procedure based upon a cross-reference of a desired power setting relative to the power setting data set and a desired lesion depth relative to the lesion depth data set.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
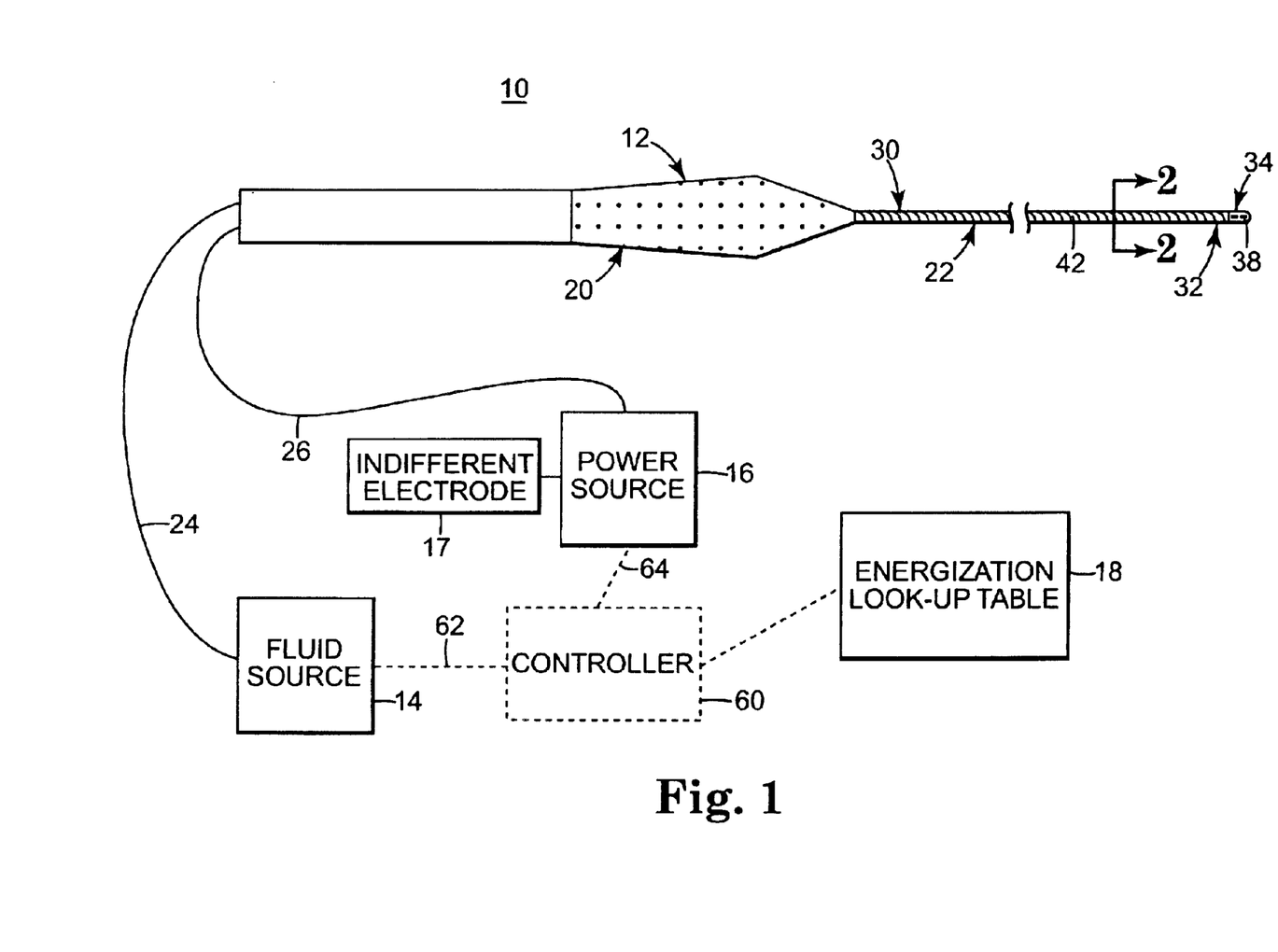
FIG. 1 is a side view of an electrosurgical system in accordance with the present invention, including the portion shown in block form.

One preferred embodiment of an electrosurgical system 10 in accordance with the present invention is shown in FIG. 1. The system 10 is comprised of an electrosurgical instrument 12, a fluid source 14, a power source 16, an indifferent electrode 17, and an energization look-up table 18. The various components are described in greater detail below. In general terms, however, the fluid source 14 is fluidly connected to the electrosurgical instrument 12. Similarly, the power source 16 is electrically connected to the electrosurgical instrument 12. During use, conductive fluid is delivered from the fluid source 14 to a distal portion of the electrosurgical instrument 12. The distributed fluid is energized by the electrosurgical instrument 12 via the power source 16 and the indifferent electrode 17. The so-energized conductive fluid is capable of forming a virtual electrode, which is capable of ablating or cauterizing tissue. Finally, the energization look-up table 18 is referenced to determine a recommended energization time period for activation of the electrosurgical instrument 12 as detailed below.

One preferred embodiment of the electrosurgical instrument 12 includes a handle 20 and a shaft 22. The handle 20 is preferably constructed of a sterilizable, rigid, and non-conductive material, such as polymer or ceramic. Suitable polymers include rigid plastic, rubber, acrylic, nylon, polystyrene, polyvinylchloride, polycarbonate, polyurethane, polyethylene, polypropylene, polyamide, polyether, polyester, polyolefin, polyacrylate, polyisoprene, fluoropolymers, combinations thereof, or the like. The handle 20 forms one or more central lumens (not shown). The lumen(s) provides a pathway for a line or tubing 24 from the fluid source 14 to the shaft 22, as well as a pathway for a line or wiring 26 from the power source 16 to the shaft 22.

The shaft 22 is rigidly coupled to the handle 20, and is an elongated, relatively rigid tubular component defining a proximal section 30 and a distal section 32. The distal section 32 terminates in an electrically conductive tip (or electrode) 34. The tip 34 may be rounded, defining a uniform radius of curvature, or it may have a more angular shape. In addition, the tip 34 may comprise one or more materials and/or components. For example, the tip 34 can have a roller ball configuration. Regardless, the electrically conductive tip 34 shape facilitates sliding movement of the tip 34 along the tissue.

Figure 2:
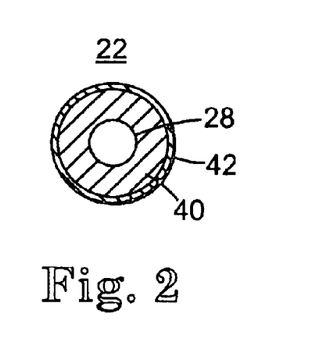
FIG. 2 is an enlarged, cross-sectional view of a portion of an electrosurgical instrument of FIG. 1 taken along the line 2—2.

With additional reference to FIG. 2, the shaft 22 defines an internal lumen 28 that is fluidly connected to the tube 24 that is otherwise fluidly connected to the fluid source 14. In this way, fluid is delivered from the fluid source 14 to the distal section 32 via the internal lumen 28.

The distal section 32 preferably forms at least one passage (referenced generally at 38 in FIG. 1) that is fluidly connected to the internal lumen 28. The at least one passage 38 is formed at or proximal to the tip 34. The at least one passage 38 provides a relatively uniform disbursement of conductive fluid about tip 34 via the internal lumen 28. In a preferred embodiment, a plurality of the passages 38 are provided along a circumference of the distal section 32, as well as a passage (not shown) at the tip 34. With this one preferred embodiment, the plurality of passages 38 are circumferentially aligned, and uniformly spaced. Effectively, then, the distal section 32, and in particular the tip 34, is porous. Alternatively, the number(s) and locations(s) of the passage(s) 38 can assume any other form sufficient for distributing fluid from the internal lumen 28.

In one preferred embodiment, the shaft 22 includes an elongated electrode body 40 and an electrical insulator covering 42 as shown in FIGS. 1 and 2. The electrode body 40 defines the proximal section 30 and the distal section 32 of the shaft 22. To this end, the proximal section 30 of the electrode body 40 is rigidly coupled to the handle 20. The insulator 42 covers a substantial portion of the electrode body 40, preferably leaving the distal section 32 exposed. In particular, the insulator 42 is positioned to encompass an entirety of the electrode body 40 distal the handle 20 and proximal the distal section 32 (and in particular, proximal the at least one passage 38 and the tip 34).

In one preferred embodiment, the electrode body 40 is tube formed of an electrically conductive, malleable material, preferably stainless steel. The insulator 42 is formed of an electrical non-conductive material and serves to electrically insulate the encompassed portion of the electrode body 40.

Notably, the electrosurgical instrument 12 can assume a variety of forms known in the art, varying from that described with respect to FIG. 1. In most general terms, the electrosurgical instrument 12 includes an electrode (e.g., the tip 34) at a distal portion thereof. Regardless of the exact construction, the fluid source 14 is preferably fluidly connected to the electrosurgical instrument 12 by the tube or line 24 and maintains a supply of conductive fluid (not shown), such as an energy-conducting fluid, an ionic fluid, a saline solution, saturated saline solution, a Ringers solution, etc. It is preferred that the conductive fluid be sterile. The conductive fluid may comprise one or more contrast agents and/or biological agents such as a diagnostic agent, therapeutic agent or drug. In one preferred embodiment, the fluid source 14 includes a fluid reservoir, such as a bag, bottle or canister, for maintaining a supply of conductive fluid. With this configuration, the fluid reservoir is positioned at an elevated location, thereby gravity feeding the conductive fluid to the electrosurgical instrument 12 via the tube 24. Alternatively, the fluid reservoir may be pressurized, thereby pressure feeding the conductive fluid to the electrosurgical instrument 12. Even further, the fluid source 14 may include, and/or be connected to, a manual or electric pump.

The power source 16 is electrically connected to the electrosurgical instrument 12 by the wire or line 26 and is of a type known in the art, preferably a radiofrequency (RF) generator. The generator may be powered by AC current, DC current, or it may be battery powered either by a disposable or re-chargeable battery. The power source 16 can assume a variety of forms, and is provided to selectively energize the electrode tip 34. To this end, the power source 16 is preferably configured to have a multitude of available power settings.

It will be recognized that the above-described electrosurgical instrument 12, fluid source 14, and power source 16 are but a few examples of acceptable configurations. In general terms, essentially any electrosurgical instrument can be used with the present invention, and in particular in combination with the energization look-up table 18. To this end, the success of most electrosurgical procedures employing energized conductive fluid is dependent upon lesion depth, power setting, irrigation rate, and energization time. The first factor (lesion depth) is a function of the remaining three factors that are otherwise controlled by the surgeon. Previously, a surgeon was required to simply guess as to appropriate settings/times for power, irrigation rate and energization time, unnecessarily lengthening the overall procedure time. The present invention overcomes this distinct drawback by incorporating the energization look-up table 18, either as a discrete table available for referral by the surgeon, or in electronic form in a manner that assists in controlling operation of the electrosurgical instrument 12, the fluid source 14 and/or the power source 16.

Figure 3:
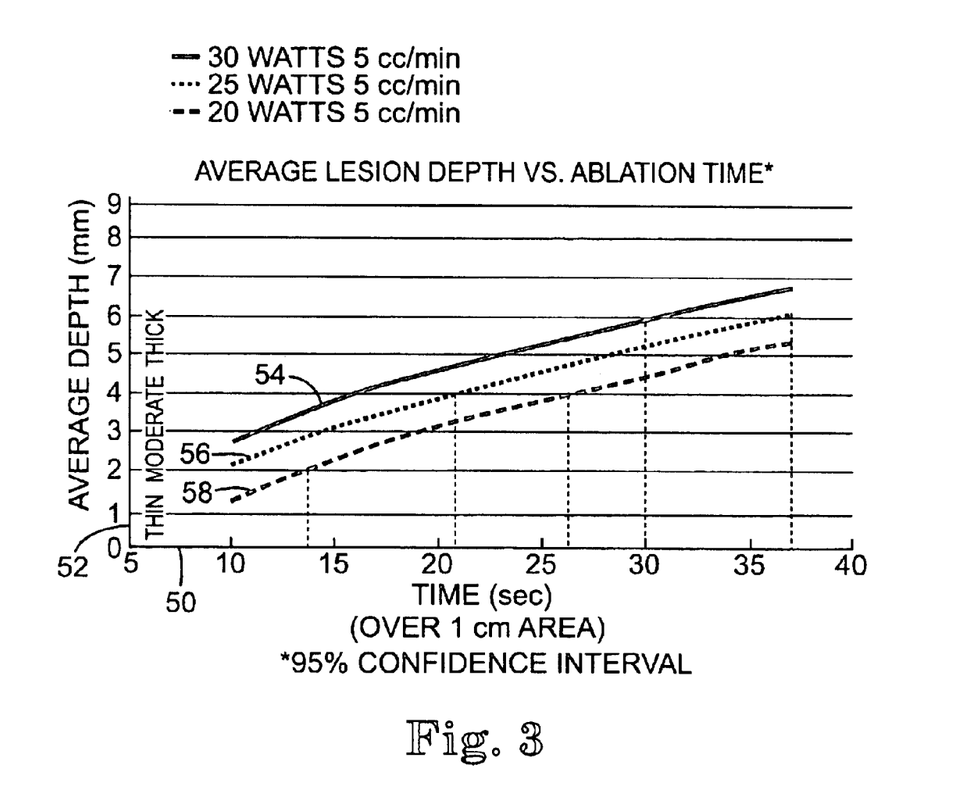
FIG. 3 is an example of an energization look-up table in accordance with the electrosurgical system of FIG. 1.

As illustrated in FIG. 3, the energization look-up table 18 provides predetermined length of time information and is preferably an organized collection of previously collected data correlating the interaction between the following four variables: a lesion depth, a power setting, an irrigation rate, and an energization time. In general terms, the predetermined length of time information embodied by the look-up table 18 correlates a plurality of lesion depth values with a plurality of power setting values, and identifies an energization time period value for each lesion depth value and power setting value. The preferred look-up table 18 allows a user to apply two, more preferably three, of the four variables to ascertain the fourth. Most commonly, the lesion depth, power setting and the irrigation rate are applied to the look-up table 18 to ascertain the corresponding energization time (or a recommended energization time period for the particular procedure to be performed).

In one preferred embodiment, the look-up table 18 is a graphical representation of the four variables. An X-axis 50 of the look-up table 18 corresponds to energization time period information, a Y-axis 52 corresponds to a lesion depth data set, and a first power setting data set is plotted in series 54 with respect to the X-axis 50 and the Y-axis 52. A second power setting data set is also plotted in series 56 and a third power setting data set is plotted in series 58. The one exemplary look-up table 18 provides recommended energization time periods for forming a 1 cm long lesion, as described below, to the desired lesion depth at a 95% confidence level. That is to say, a surgeon who has a desired lesion depth and selected power setting can refer to the table 18 and ascertain a correspondingly, recommended energization time and know that the recommended time has proven to achieve the desired results (i.e., desired results (i.e., desired lesion depth) with a 95% confidence level. In a further preferred embodiment, the look-up table 18 is adapted to provide energization time period information that has a 95% confidence bound on an upper limit of lesion depth. The one preferred look-up table 18 provided in FIG. 3 incorporates this upper bound, such that a recommended energization time period delivered from the table 18 will not result in too deep a lesion. Alternatively, the table 18 can be adapted to correspond to longer or shorter lesion lengths. Further, a plurality of different look-up tables 18 are preferably provided, with each corresponding to a different irrigation rate and/or for different types of tissue, such as heart tissue, liver tissue, prostate tissue, etc. Thus, for example, a first look-up table can be provided that embodies a correlation of lesion depth values with power setting values, along with a second (or third, etc.) look-up table that correlates lesion depth values with power setting values for a second irrigation rate. Notably, the look-up table 18 may incorporate the variables in other organizational methods (e.g., lesion depth versus power setting; a tabular representation of individual lesion depth, power setting, and time period values, etc.) and/or or need not reflect a particular irrigation rate, and remain within the scope of the present invention.

In a preferred embodiment, the look-up table 18 is provided apart from the electrosurgical instrument 12, such as in hard paper form. Alternatively, a computer or similar device can be employed to display the desired look-up table 18. In another embodiment, however the electrosurgical system 10 further includes a controller 60. The controller 60 is preferably electrically connected to the fluid source 14 by a line or wire 62 and to the power source 16 by a line or wire 64, and is preferably a microprocessor-based computer including associated memory and input/output circuiting. Alternatively, a programmable logic controller (PLC) or other controller or equivalent circuitry can be employed. Regardless, the controller 60 stores the look-up table 18 and the corresponding data sets. The controller 60 is adapted to convert two, or preferably three variables (i.e., lesion depth, power setting, and/or irrigation rate) inputted by a user (e.g., via a keyboard) into a recommended energization time period value by referencing the internal look-up table 18. The controller 60 is further preferably adapted to adjust the irrigation rate of the fluid source 14 and the power setting of the power source 16 as needed or dictated by a user, and control activation/deactivation of the power source 16 in accordance with the determined recommended energization time period.

Figure 4:
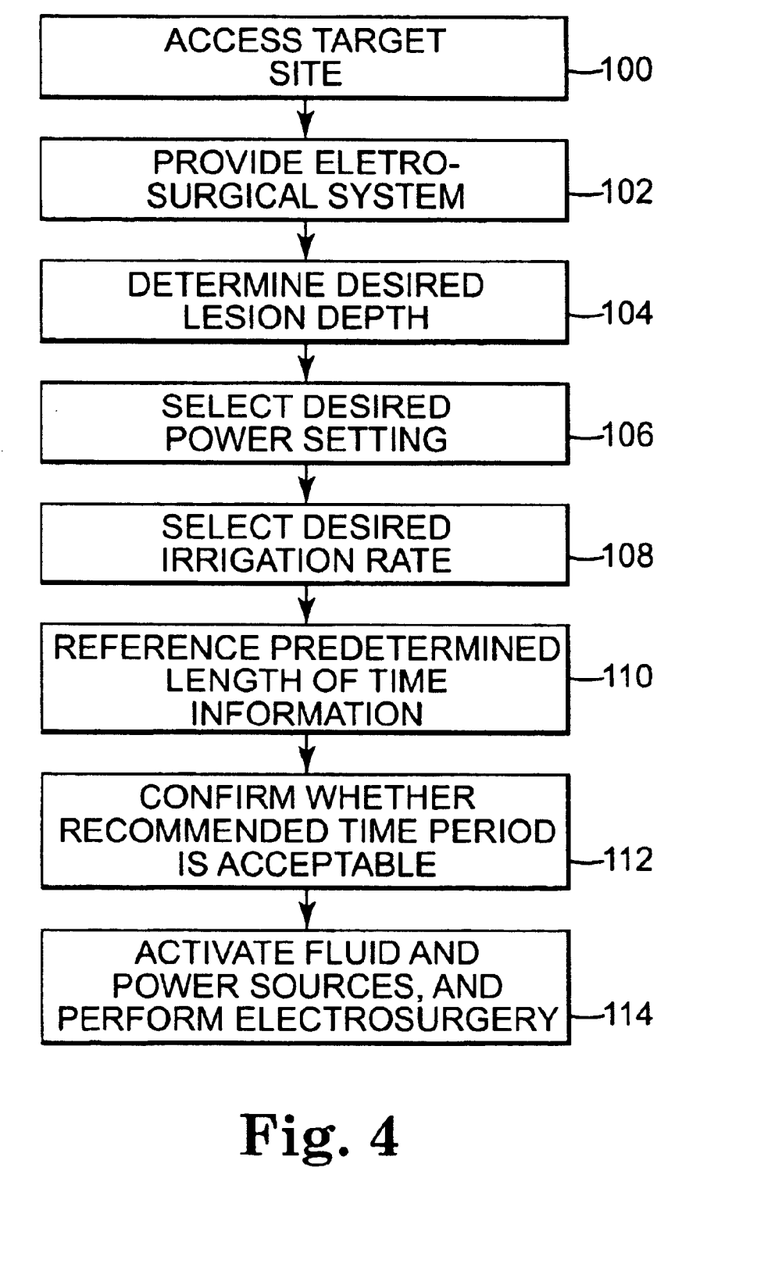
FIG. 4 is a flow diagram illustrating a method of use for the electrosurgical system of FIG. 1 in accordance with the present invention.

The flow diagram of FIG. 4 illustrates one preferred method of forming a lesion on living tissue in accordance with the present invention. As a point of reference, the above-described electrosurgical system 10, including the electrosurgical instrument 12 is useful for a number of different tissue ablation and cauterization procedures. For example, the system 10 can be used to remove hemorrhoids or varicose veins, or stop esophageal bleeding to name but few possible uses. Additionally, the system 10 is highly useful for the surgical treatment of cardiac arrhythmia, and in particular treatment of atrial fibrillation, via ablation of atrial tissue. With this in mind, the methodology of FIG. 4 is described in conjunction with an ablation (or lesion forming) procedure performed on atrial tissue as shown in FIG. 5, it being understood that the technique is equally applicable to a variety of other electrosurgical procedures. Prior to performing the electrosurgical procedure, it is assumed that the surgeon has evaluated the patient and determined that the specific procedure to be appropriate for the individual patient.

Figure 5A:
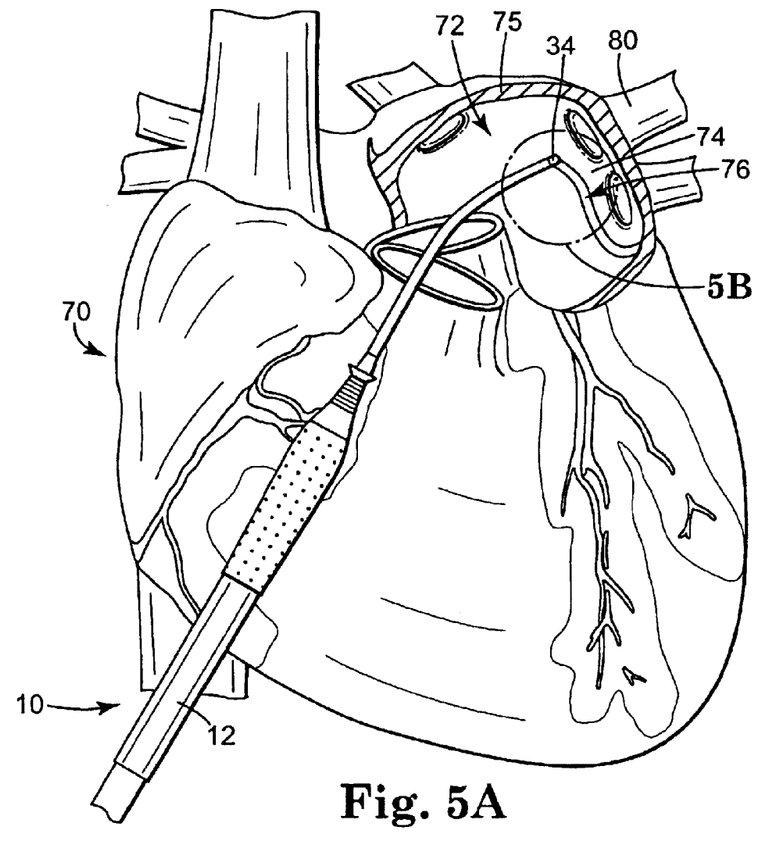
FIG. 5A is a cut-away illustration of a patient's heart depicting use of the electrosurgical system of FIG. 1 during a surgical procedure.
Figure 5B:
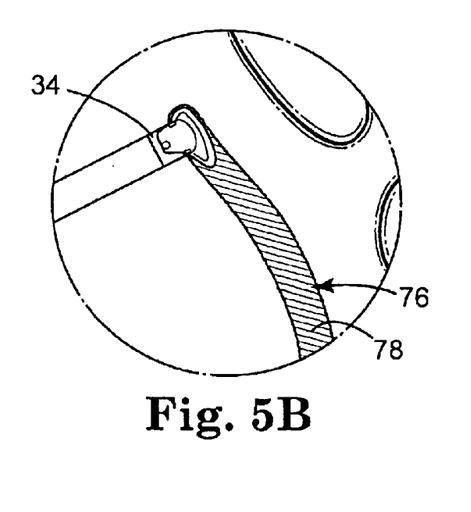
FIG. 5B is an enlarged illustration of a portion of the view of FIG. 5A.

With the one preferred atrial application reflected in FIGS. 5A and 5B, a portion of a Maze procedure is performed. In particular, FIG. 5A includes a representation of a heart 70 with its left atrium 72 exposed. In this regard, step 100 of FIG. 4 delineates that access to a target site 74 is gained. Relative to the one exemplary procedure of FIG. 5A, the target site 74 is accessed by splitting the patient's sternum (not shown) and opening the patient's rib cage (not shown) with a retractor. Various incision are then made into the heart 70 to expose an interior of the left atrium 72. Of course, other techniques are available for accessing the target site 74. Further, access to a particular target site 74 could be gained, for example, via a thoractomy, sternotomy, percutaneously, transveneously, arthroscopically, endoscopically, for example through a percutaneous port, stab wound or puncture through a small incision (e.g., in the chest, groin, abdomen, neck, or knee), etc. In addition, it is possible to gain access to the outside of the heart 70 from within the heart 70. For example, a catheter device may be passed from an interior of the heart 70, through an appendage wall of the heart 70, to an exterior of the heart 70. As described below, the electrosurgical instrument 12 may then be manipulated to contact an epicardial surface of the heart 70.

At step 102, the electrosurgical system 10 is provided. As previously described, the system 10 includes the electrosurgical instrument 12, the power source 16, the fluid source 14, and the look-up table 18. In one preferred embodiment, the system 10 also includes the controller 60.

At step 104, a desired lesion depth is determined. To determine the desired lesion depth, the target tissue site 74, such as a portion of an atrial wall 75 of the heart 70 as illustrated in FIG. 5A, is identified and evaluated to determine its thickness. The desired lesion depth is then determined based upon the determined thickness, as the thickness is proportionate to the desired lesion depth. The actual proportion utilized, however, depends upon the requirements of the particular electrosurgical procedure being performed. For example, in an electrosurgical procedure to correct atrial fibrillation, such as a Maze procedure, a transmural lesion is required, and consequently, the desired lesion depth will be equal to the thickness of the target site tissue 74. Of course, other electrosurgical procedures may entail a desired lesion depth that is less than the evaluated thickness of the target site 74, for example, by a prescribed percentage (e.g., 50% of the target site 74 thickness).

At step 106, a desired power setting for the power source 16 is selected. The power setting mandates how much heat is created within the target tissue site 74 during a subsequent electrosurgical procedure. As a starting point, it will be understood that for most electrosurgical procedures, certain recommended protocols have been developed, and are available to the surgeon. These protocols provide guidelines or accepted ranges for certain procedure parameters, including power setting. Thus, when selecting a desired power setting for a particular procedure, the surgeon will initially refer to recommended power settings. Then, with this prescribed range in mind, to determine the specific power setting for a particular electrosurgical procedure, the risks associated with a probable energization time and a probability of "pops" are considered.

A shorter ablation time generally corresponds with a lower risk of complications, since lesions can be closed sooner, and consequently, the body can be returned to a relatively natural state in a shorter period of time thereby reducing the chance of infection, thromboembolism, or other complications. Therefore, since a higher power setting creates the lesion in a shorter period of time, a higher power setting within the recommended range for a particular procedure is preferred in consideration of energization time.

However, the higher the power setting, the higher the probability of "pops". A pop occurs when the target site tissue 74 is heated so rapidly that intracellular fluid within the target site tissue 74 begins to boil and the target site tissue 74 erupts causing damage to the tissue. Although a majority of the pops are relatively small and require no further surgical intervention, larger pops can require suturing and may thereby damage the tissue strength and prolong the length of the electrosurgical procedure. As a result, a goal of the electrosurgical procedure is to minimize, or at least decrease, the occurrence of pops. Since the higher power setting increases the probability of pops, a lower power setting is desired in consideration of the probability of pops.

Therefore, in selecting the desired power setting, a surgeon considers the probable energization time and the probability of pops to determine the power setting that will minimize the combined risks involved in the electrosurgical procedure.

At step 108, a desired irrigation rate of the fluid source 16 is selected. The irrigation rate affects the amount and rate of heat generated in the target tissue site 74. If the irrigation rate is too low, the tissue will heat too quickly increasing the probability of pops and/or causing dry ablation/electrocauterization that may result in the build-up of excess charred tissue on the electrode tip 34 of the electrosurgical instrument 12, decreasing the overall performance of the electrosurgical system 10. For example, tissue char will raise the impedance of the tissue, thereby preventing the creation of a deep lesion. The decreased level of performance requires the tip 34 to be cleaned on a piece of sterile gauze or the like and, consequently, increases the chance of incision contamination. Conversely, if the irrigation rate is set too high, it will overcool the target tissue site 74 increasing the time needed to create a lesion and slow the electrosurgical procedure. As a point of reference, ablation of atrial tissue typically entails an irrigation rate of 3 to 10 cc/minute, more preferably an irrigation rate of 5 ccs per minute. Of course, other procedures can have varying irrigation rate guidelines.

Although step 108 is illustrated in FIG. 4 as following step 106, steps 106 and 108 may be performed in the opposite sequence or relatively simultaneously.

At step 110, the predetermined length of time information embodied in the look-up table 18 is referenced to determine a recommended energization time period. In one preferred embodiment, a surgeon or assistant chooses the look-up table 18 that corresponds with the desired irrigation rate selected at step 108. The desired lesion depth, determined at step 104, and the selected power setting, determined at step 106, are then applied to the look-up table 18 to determine the corresponding recommended energization time period needed to create an appropriate lesion 76 (referenced generally in FIG. 5A) in the target site tissue 74.

In one example, the desired lesion depth is 4 mm, the selected power setting is 25 watts, and the selected irrigation rate is 5 cc/minute. Under these constraints, reference to the look-up table 18 illustrated in FIG. 3 provides a recommended energization time period of 20.7 seconds. Preferably, the energization time information corresponds with a lesion length of 1 cm. However, the look-up table 18 can be adapted to provide energization time period information corresponding with other lesion lengths. Additionally or alternatively, a surgeon can extrapolate the recommended energization time period information for a 1 cm lesion length to arrive at an appropriate energization time period for the particular procedure/lesion being performed.

At step 112, the surgeon determines whether or not the combined risks are acceptable. The surgeon compares the selected power setting and irrigation rate previously determined at steps 106 and 108, respectively, to the recommended energization time period determined at step 110 to ensure all values interact in a manner that produces an acceptable combined risk of complication. If the recommended energization time period is not acceptable based upon consideration of the selected power setting and the resultant procedure time, the surgeon repeats steps 106 through 112 until the combined risks are acceptable. Once the combined risks are acceptable, the surgeon continues to step 114.

At step 114, fluid flow from the fluid source 14 is initiated and the power source 16 is activated, and the electrosurgical instrument 12 (in particular the electrode tip 34) is applied to the target tissue site 74 to create the lesion 76, as best shown in FIG. 5B. In one preferred embodiment, liquid flow from the fluid source 14 is initiated for a short time period prior to activation of the power source 16 to ensure that liquid is being distributed to the target site 74 before energy is applied. The electrode tip 34 is then evenly drawn (preferably in a back-and-forth motion) across the target tissue site 74 over the length corresponding to the recommended energization time period (e.g., 1 cm), determined at step 110, to create the lesion 76 with the desired lesion depth. The electrosurgical device 12 may be manipulated by a surgeon and/or by a robot. As for the previously described example, the electrosurgical instrument 12 with the selected power setting at 25 watts and the selected irrigation rate at 5 cc/minute is evenly drawn across a 1 cm length of tissue for 20.7 seconds to create the lesion 76 having the lesion depth of 4 mm.

Step 114 may be repeated from an end of the newly formed lesion 76 to form a second lesion (preferably having a length corresponding with a length of the first lesion 76) until a number of lesions have been created to form a desired pattern 78 for the particular electrosurgical procedure being performed. Each lesion segment is preferably formed at the same selected power setting and recommended irrigation rate, utilizing the recommended energization time period. With the one example illustrated in FIG. 5, the lesion pattern 78 is formed on a left atrial wall 72 of the heart 70 and encircles two right pulmonary veins 80 as a step in a Maze procedure.

The procedure described above does not incorporate the optional controller 60 (FIG. 1). If the electrosurgical system 10 includes the controller 60, steps 106 through 112 can be completed by or with the assistance of the controller 60. To this end, the controller 60 can be adapted to provide varying levels of control over the electrosurgical instrument 12, the fluid source 14, and/or the power source 16. For example, the controller 60 may display the applicable look-up table 18, with the surgeon having complete, independent control over the components 12–16. Alternatively, the controller 60 may be adapted to automatically initiate and/or control fluid flow from the fluid source 14 at the selected irrigation rate. Further, the controller 60 may be adapted to automatically deactivate the power source 16 at the completion of the energization time. Also, the controller 60 may be adapted to provide an audible and/or visible signal or warning (e.g., flashing lights, buzzer, etc.) during the procedure, or at or near the expiration of the recommended energization time period. For example, the controller 60 may be adapted to operate a sound-producing device in a manner that provides an audible signal in pre-determined increments (e.g., once per second) while power is on, thereby acting like a metronome to aid in timing the preferred back-and-forth motion of the electrosurgical instrument 12, and in particular the tip 34.

As previously described, the electrosurgical procedure is highly useful for the surgical treatment of atrial fibrillation, via ablation of atrial tissue, for example as part of the Maze procedure. The Maze procedure, such as described in *Cardiovascular Digest Update*, Vol. 1, No. 4, July 1995, pp. 2–3, the teachings of which are incorporated herein by reference, is a well-known technique whereby lesion patterns are created along specified areas of the atria. The Maze III procedure, a modified version of the original Maze procedure, has been described in *Cardiac Surgery Operative Technique*, Mosby Inc., 1997, pp. 410–419, the teachings of which are incorporated by referenced. In an effort to reduced the complexity of the surgical Maze procedure, a modified Maze procedure was developed in *The Surgical Treatment of Atrial Fibrillation*, Medtronic Inc., 2001, the teachings of which are incorporated herein by reference. In general terms, the system and method of the present invention may be employed to form one or all of the lesions/lesion patterns required by the above-identified surgical procedures. For example, the look-up table 18 may be referenced, and the recommended energization time period employed to form lesions on the tricuspid annulus in the right atrium, the coronary sinus, the mitral valve annulus in the left atrium, etc.

The electrosurgical system and method of the present invention provides a marked improvement over previous protocols. In particular, by utilizing predetermined length of time information that otherwise correlates lesion depth and power setting with energization time, embodied by one or more look-up tables, a surgeon can determine a recommended energization time period prior to applying the electrosurgical instrument to the target tissue site. Knowledge of the energization time period decreases the requirement of constant measurement and testing during the electrosurgical procedure and, consequently, reduces the time required to create the lesion having the desired properties. Reduction of the surgical time reduces the risk of complication, accordingly.

Although the present invention has been described with reference to preferred embodiments, workers skilled in the art will recognize that changes can be made in form and detail without departing from the spirit and the scope of the present invention.

What is claimed is:

1. An electrosurgical system for performing an electrosurgical procedure, the electrosurgical system comprising:
   an electrosurgical instrument having a handle, an elongated shaft extending from the handle and an electrode on the shaft, wherein the shaft is characterized as being more rigid than a catheter for manipulating the electrode to engage tissue in a drawn back-and-forth manner;
   a power source having multiple available power settings and being electrically connected to the electrosurgical instrument for selectively energizing the electrode; and
   a controller for electronically selecting a recommended energization time period by reference to predetermined length of time information that relates to the electrosurgical instrument and based upon a power setting selected prior to energizing the electrode at a power level to minimize the possibility of pops and a desired lesion depth.

2. The system of claim 1, wherein the electrosurgical device includes an internal lumen fluidly connected to at least one passage formed in the electrode, and wherein the electrosurgical system further includes:
   a fluid source fluidly connected to the internal lumen, the fluid source being configured to supply a liquid to the at least one passage at a selected irrigation rate during the electrosurgical procedure.

3. The system of claim 2, wherein the controller is further adapted to determine the recommended energization time period based upon the selected irrigation rate.

4. The system of claim 1, wherein the controller is electrically connected to the power source and is adapted to automatically deactivate the power source upon completion of the recommended energization time period.

5. An electrosurgical system for performing an electrosurgical procedure on living tissue, the system comprising:
   an electrosurgical instrument having an electrode at a distal portion;
   a power source having multiple available power settings and being electrically connected to the electrosurgical instrument for selectively energizing the electrode; and
   an energization look-up table corresponding with the electrosurgical instrument, the
   energization look-up table including:
      a power setting data set that includes a least one of the multiple available power settings,
      a lesion depth data set,
      energization time period information organized as a function of the power setting and lesion depth data sets, and
      energization time period values for an electrode being drawn back-and-forth across tissue as a function of power and lesion depth.

6. An electrosurgical system for performing an electrosurgical procedure on living tissue, the system comprising:
   an electrosurgical instrument having a handle, an elongated, insulated shaft rigidly extending from the handle and an electrode on the shaft, the electrode spaced from the handle, the instrument adapted to create a linear lesion having a length on the tissue by grasping the handle and manipulating the rigidly connected electrode to contact the tissue with a drawn back-and-forth motion along the length;
   a power source having multiple available power settings and being electrically connected to the electrosurgical instrument for selectively energizing the electrode; and
   an energization look-up table corresponding with the electrosurgical instrument, the energization look-up table including:
      a power setting data set that includes at least two of the multiple available power settings of the power source,
      a lesion depth data set,
      energization time period information organized as a dependent variable of the power setting and lesion depth data sets;
   wherein the energization look-up table is adapted to identify a recommended energization time period and power setting based upon a desired lesion depth by a cross-reference between energization time and power setting for minimizing a possibility of pops during an electrosurgical procedure.

7. The system of claim 6, further including:
   a fluid source fluidly connected to an internal lumen of the electrosurgical instrument, the fluid source being configured to supply a liquid to a region of the electrode at an irrigation rate during an electrosurgical procedure.

8. The ablation system of claim 7, wherein the energization look-up table correlates the energization time period information with a desired irrigation rate.

9. The system of claim 6, wherein the system further comprises:
   a controller electronically storing the energization look-up table, wherein the controller is adapted to convert the selected power setting and the desired lesion depth into a recommended energization time period based upon reference to the energization look-up table.

10. The system of claim 9, wherein the controller is electrically connected to the power source, and further wherein the controller is configured to control the power setting of the power source.

11. The system of claim 10, wherein the controller is adapted to automatically deactivate the power source upon completion of the recommended energization time period.

12. A method of making a lesion at living tissue at a target site, the method comprising:
   providing an electrosurgical system including:
      an electrosurgical instrument having an electrode at a distal portion, and
      a power source having multiple available power settings, wherein the power source is electrically connected to the electrode;
   determining a desired depth for the lesion;
   selecting a desired power setting for the power source, including considering a probability of PODS during a subsequent electrosurgical procedure; and
   applying electrical energy to the electrode in contact with the living tissue, the energy applied to the living tissue at the desired power setting for a recommended energization time period determined by reference to predetermined length of time information and based upon the desired lesion depth and the selected power setting;

wherein the step of selecting a desired power setting is completed prior to determining the recommended energization time period, and the recommended energization time period is determined prior to the step of applying electrical energy to the electrode.

13. The method of claim 12, wherein the predetermined length of time information correlates a plurality of lesion depth values with a plurality of power setting values and identifies an energization time period value for each lesion depth value and power setting value combination.

14. The method of claim 13, wherein the recommended energization time period is determined by ascertaining the energization time period value identified by the predetermined length of time information that otherwise corresponds with the desired lesion depth and the selected power setting combination.

15. The method of claim 14, wherein the predetermined length of time information is embodied in a look-up table.

16. The method of claim 14, wherein the predetermined length of time information includes an algorithm.

17. The method of claim 14, wherein the electrosurgical instrument is further configured to distribute a liquid from a fluid source to a region of the electrode at a plurality of irrigation rates, and further wherein the predetermined length of time information is generated as a function of irrigation rate.

18. The method of claim 17, further comprising selecting a desired irrigation rate prior to the step of applying electrical energy and irrigating the electrode with the liquid during the step of applying electrical energy.

19. The method of claim 18, wherein the recommended energization time period is further determined based upon the selected irrigation rate.

20. The method of claim 19, wherein the predetermined length of time information includes a first correlation of lesion depth values with power setting values for a first irrigation rate and a second correlation of lesion depth values with power setting values for a second irrigation rate.

21. The method of claim 20, wherein the predetermined length of time information includes a first look-up table embodying the first correlation and a second look-up table embodying the second correlation.

22. The method of claim 12, wherein determining a desired lesion depth includes:

estimating a thickness of the target tissue area.

23. The method of claim 12, wherein selecting a desired power setting further includes:

considering a probable period of time for making the lesion.

24. The method of claim 23, wherein selecting a desired power setting further includes:

balancing a first risk associated with the probability of pops and a second risk associated with the probable period of time.

25. The method of claim 12, wherein the predetermined length of time information corresponds to a length of time needed for the electrosurgical system to create a lesion having a length of 1 cm.

26. The method of claim 12, further comprising:

drawing the electrode back and forth across the target tissue site during the step of applying electrical energy.

27. The method of claim 26, wherein the step of drawing the electrode back and forth results a first lesion segment upon completion of the recommended energization time period, the method further comprising forming a second lesion segment connected to the first lesion segment to define a lesion pattern.

28. The method of claim 27, wherein the lesion pattern is created as a part of a Maze procedure.

29. The method of claim 12, wherein the electrosurgical system further includes a controller storing the predetermined length of time information, and further wherein the recommended energization time period is determined by:

operating the controller to reference the predetermined length of time information.

30. The method of claim 29, wherein the controller includes an input device and a display device, and further wherein operating the controller includes:

inputting the desired lesion depth and the selected power setting via the input device;

automatically applying the desired lesion depth and the selected power setting to the predetermined length of time information to determine the recommended energization time period; and displaying the recommended energization time period via the display device.

31. The method of claim 29, wherein the controller further includes a warning device, the method further comprising:

activating the warning device upon completion of the recommended energization time period.

32. The method of claim 12, wherein the step of selecting a desired power setting is performed by a surgeon.

33. A method of making a lesion at living tissue at a target site, the method comprising:

providing an electrosurgical system including:

an electrosurgical instrument having an electrode at a distal portion, and a power source having multiple available power settings, wherein the power source is electrically connected to the electrode;

determining a desired depth for the lesion;

selecting a desired power setting for the power source;

determining a recommended energization time period by reference to predetermined length of time information and based upon the desired lesion depth and the selected power setting;

contacting the living tissue at the target site with the electrode; and applying electrical energy to the electrode at the selected powered setting for the recommended energization time period while drawing the electrode back-and-forth across the living tissue at the target site.

34. The method of claim 33, wherein determining a recommended energization time period includes accounting for movement of the electrode.

* * * * *

UNITED STATES PATENT AND TRADEMARK OFFICE
CERTIFICATE OF CORRECTION

PATENT NO. : 6,827,715 B2 Page 1 of 1
APPLICATION NO. : 10/056806
DATED : December 7, 2004
INVENTOR(S) : Francischelli et al.

It is certified that error appears in the above-identified patent and that said Letters Patent is hereby corrected as shown below:

Column 12, line 62, that portion of the claim reading "of PODS" should read --of pops--.

Signed and Sealed this

Twentieth Day of March, 2007

JON W. DUDAS
*Director of the United States Patent and Trademark Office*